US009995716B2

(12) United States Patent
Brignac et al.

(10) Patent No.: US 9,995,716 B2
(45) Date of Patent: Jun. 12, 2018

(54) METHOD FOR DETERMINING BOILER TUBE COLD SIDE CRACKING AND ARTICLE FOR ACCOMPLISHING THE SAME

(71) Applicant: Alstom Technology Ltd, Baden (CH)

(72) Inventors: Jacques L. Brignac, Simsbury, CT (US); Larry D. Kidd, Ooltewah, TN (US); Robert Lucas, Soutbury, CT (US); Christopher Curl, Branford, CT (US)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 683 days.

(21) Appl. No.: 13/650,763

(22) Filed: Oct. 12, 2012

(65) Prior Publication Data
US 2014/0102201 A1    Apr. 17, 2014

(51) Int. Cl.
*G01N 29/24* (2006.01)
*G01N 29/04* (2006.01)
*G01N 29/22* (2006.01)

(52) U.S. Cl.
CPC ......... *G01N 29/041* (2013.01); *G01N 29/043* (2013.01); *G01N 29/225* (2013.01);
(Continued)

(58) Field of Classification Search
CPC ..... G01N 2291/2634; G01N 2291/106; G01N 29/265; G01N 2291/044; G01N 29/28;
(Continued)

(56) References Cited

U.S. PATENT DOCUMENTS

| 2,956,185 A * | 10/1960 | Von Stocker .......... G01N 29/28 310/336 |
| 4,195,530 A | 4/1980 | Ross et al. |

(Continued)

FOREIGN PATENT DOCUMENTS

| CN | 101256173 A | 9/2008 |
| CN | 101368932 A | 2/2009 |

(Continued)

OTHER PUBLICATIONS

Unofficial English translation of Japanese Office Action issued in connection with corresponding JP Application No. 2015120972 dated Jun. 14, 2016.
(Continued)

*Primary Examiner* — Helen Kwok
*Assistant Examiner* — Nashmiya Fayyaz
(74) *Attorney, Agent, or Firm* — GE Global Patent Operation; Stephen G. Midgley

(57) ABSTRACT

Disclosed herein is a scanning device for performing ultrasonic nondestructive testing of a tube, comprising a housing; the housing having bottom surface that is concavely curved with cavities to accommodate a waveguide assembly and an encoder assembly; where the waveguide assembly comprises a waveguide and a probe that are in communication with one another; the waveguide having at least one surface that is contoured to match an outer surface of the tube; where the waveguide facilitates the transmission of ultrasonic signals into the tube generated by the probe; and where the encoder assembly comprises a spring loaded wheel that contacts the tube; and where the encoder assembly provides a signal indicative of a location of the probe relative to a position on the tube as the scanning device is moved in a direction of a longitudinal axis of the tube.

18 Claims, 8 Drawing Sheets

(52) U.S. Cl.
CPC ..... *G01N 29/2462* (2013.01); *G01N 29/2487* (2013.01); *G01N 2291/0289* (2013.01); *G01N 2291/044* (2013.01); *G01N 2291/2634* (2013.01)

(58) Field of Classification Search
CPC ....... G01N 29/2462; G01N 2291/0289; G01N 29/041; G01N 29/2487; G01M 3/24
USPC .................................................. 73/622, 644
See application file for complete search history.

(56) References Cited

U.S. PATENT DOCUMENTS

| | | | |
|---|---|---|---|
| 4,404,853 A * | 9/1983 | Livingston | ............ E21B 17/006 73/622 |
| 5,007,291 A | 4/1991 | Walters et al. | |
| 5,035,143 A | 7/1991 | Latimer et al. | |
| 5,125,272 A | 6/1992 | Latimer et al. | |
| 5,469,743 A * | 11/1995 | Zorn | ...................... G01N 29/27 73/620 |
| 5,526,691 A | 6/1996 | Latimer et al. | |
| 5,549,004 A * | 8/1996 | Nugent | .............. G01N 29/2487 376/249 |
| 5,600,069 A | 2/1997 | Girndt et al. | |
| 6,125,703 A | 10/2000 | MacLauchlan et al. | |
| 6,138,514 A | 10/2000 | Iwamoto et al. | |
| 6,164,137 A | 12/2000 | Hancock et al. | |
| 6,578,424 B1 * | 6/2003 | Ziola | ................... G01N 29/223 73/632 |
| 6,641,535 B2 | 11/2003 | Buschke et al. | |
| 7,474,092 B1 | 1/2009 | Kwun et al. | |
| 7,984,650 B2 | 7/2011 | Brignac | |
| 8,393,217 B2 | 3/2013 | Iizuka et al. | |
| 2003/0172735 A1 | 9/2003 | Lam et al. | |
| 2003/0175735 A1 | 9/2003 | Karimova et al. | |
| 2006/0144871 A1 * | 7/2006 | Van Tuyl | ............. G01N 29/024 222/420 |
| 2009/0314089 A1 * | 12/2009 | Brignac | ............... G01N 29/226 73/622 |
| 2009/0316531 A1 | 12/2009 | Brignac | |
| 2011/0072904 A1 | 3/2011 | Lam et al. | |

FOREIGN PATENT DOCUMENTS

| | | |
|---|---|---|
| JP | S5350884 A | 5/1978 |
| JP | 59089261 U | 6/1984 |
| JP | S62-209355 | 9/1987 |
| JP | S63-113911 | 7/1988 |
| JP | H01145565 A | 6/1989 |
| JP | H01180652 U | 12/1989 |
| JP | H11248687 A | 9/1999 |
| JP | 2001-056318 | 2/2001 |
| JP | 2002-048770 | 2/2002 |
| JP | 2004 012163 | 1/2004 |
| JP | 2004514154 A | 5/2004 |
| JP | 2005168885 A | 6/2005 |
| JP | 2006170766 A | 6/2006 |
| JP | 2006337151 A | 12/2006 |
| JP | 2008145251 A | 6/2008 |
| JP | 2008209364 A | 9/2008 |
| WO | 2012003071 A1 | 1/2012 |
| WO | 2012/094383 | 7/2012 |

OTHER PUBLICATIONS

Unofficial English Translation of Japanese Search Report issued in connection with corresponding JP Application No. 2013-214403 dated Aug. 6, 2014.

Unofficial English Translation of Japanese Search Report issued in connection with corresponding JP Application No. 2015-120972 dated May 27, 2016.

* cited by examiner

SECTION A-A

SECTION B-B

SECTION C-C

METHOD FOR DETERMINING BOILER TUBE COLD SIDE CRACKING AND ARTICLE FOR ACCOMPLISHING THE SAME

FIELD OF THE INVENTION

This disclosure relates to a method for determining boiler tube cracking. In particular, this disclosure further relates to a method for determining boiler tube cold side cracking and an article for determining the same.

BACKGROUND

Boiler tube failures are a major cause of forced shutdowns in fossil fuel power plants. As a result of various operational conditions such as heat, pressure, and wear over time, boiler tubes eventually begin to fail by developing circumferential and axial cracks, as well as experience wall thinning (through both erosion and corrosion). When a boiler tube begins to leak, for example, steam escaping through the leak is lost to the boiler environment. Unless the leak is discovered and repaired, the leak may continue to grow until the tube eventually ruptures, thereby forcing the utility operating the boiler to shut it down immediately. These failures prove to be quite expensive for utilities and, as such, early boiler tube leak detection methods are highly desirable.

In boiler systems, tubes may be interconnected by welding material to form a waterwall. As a result of the construction of the tubes to form a waterwall, commercially available scanners are unable to complete a circumferential scan of the tubes. In addition, waterwall tubes are accessible from the hot side of the tubes during a shutdown. The hot side of the tubes is that side that is in direct contact with a flame and the hot gases in the boiler, while the cold side is disposed opposite to the hot side and contacts insulation. Cracking generally occurs at attachment welds at the "cold side" of the tube which is insulated and not easily accessible without insulation removal. Accordingly, it would be desirable to provide an improved scanning device for applications such as boiler tube inspection.

SUMMARY

Disclosed herein is a scanning device for performing ultrasonic nondestructive testing of a tube, comprising a housing; the housing having bottom surface that is concavely curved with cavities to accommodate a waveguide assembly and an encoder assembly; where the waveguide assembly comprises a waveguide and a probe that are in communication with one another; the waveguide having at least one surface that is contoured to match an outer surface of the tube; where the waveguide facilitates the transmission of ultrasonic signals into the tube generated by the probe; and where the encoder assembly comprises a spring loaded wheel that contacts the tube; and where the encoder assembly provides a signal indicative of a location of the probe relative to a position on the tube as the scanning device is moved in a direction of a longitudinal axis of the tube.

Disclosed herein too is a method comprising disposing upon a tube a scanning device comprising a housing; the housing having bottom surface that is concavely curved with cavities to accommodate a waveguide assembly and an encoder assembly; where the waveguide assembly comprises a waveguide and a probe that are in communication with one another; the waveguide having at least one surface that is contoured to match an outer surface of the tube; where the waveguide facilitates the transmission of ultrasonic signals into the tube generated by the probe; and where the encoder assembly comprises a spring loaded wheel that contacts the tube; and where the encoder assembly provides a signal indicative of a location of the probe relative to a position on the tube as the scanning device is moved in a direction of a longitudinal axis of the tube; contacting a surface of the tube with the waveguide; introducing ultrasonic signals into the tube at an incident angle of 20 degrees to 40 degrees with respect to the probe centerline; and where the ultrasonic signals travel through the wall thickness in the circumferential direction; retrieving the ultrasonic signals through the waveguide when the ultrasonic signals contact a crack in the tube; and analyzing the ultrasonic signals to determine the location of cracks in the tube.

DETAILED DESCRIPTION

Figure 1A:
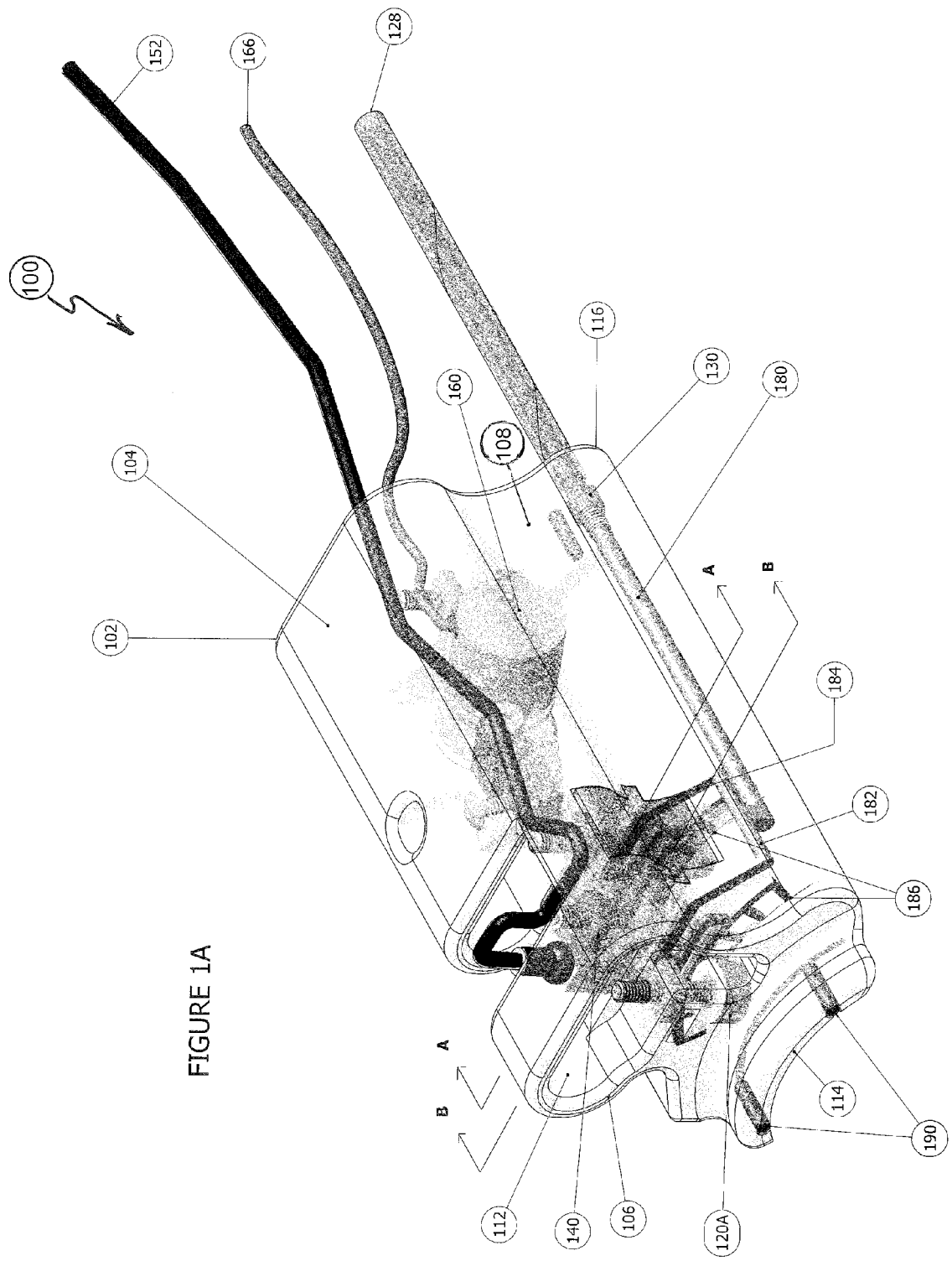
FIG. 1A is an isometric side view of an exemplary scanning device.

Disclosed herein is a portable scanning device for non-destructive testing of tubes. The tubes are part of a waterwall and are generally used in boilers and furnaces. The scanning device is compact and easily adaptable for use with tubes having different diameters, and is particularly useful for scanning waterwall tubes in steam generators (boilers). In one embodiment, the portable scanning device is used to determine cracks that occur at attachment welds located on the cold side of the waterwall tube, particularly those cracks that occur at attachment welds, which is generally insulated and therefore not easily accessible without insulation removal.

As defined herein the term "tube" includes an enclosed channel through which fluids can be transported. The closed channel can have any desired geometrical shape (when measured perpendicular to an axial direction of the conduit) and may have a circular, oval, square, or rectangular cross-sectional area. The axial direction is also referred to herein as the longitudinal direction and is measured along the length direction of the conduit.

Disclosed herein too is a method that permits crack detection on the "cold side" of waterwall tubing when the portable scanning device contacts the "hot side" of the waterwall tubing. In one embodiment, the method permits axial crack detection on the cold side of water wall tubing, when the scanning device contacts the hot side of the waterwall tubing. The method comprises introducing sound waves into a waveguide that is machined to contact a portion of the tubes outside surface. The sound waves are in the ultrasonic frequency range (hereinafter referred to as "ultrasonic signals"). The ultrasonic signals exit the waveguide material and are refracted into the tube at multiple angles based on Snell's law. The ultrasonic signal is a phased array signal and is introduced into the tube wall in a manner that facilitates the detection of corrosion fatigue and cracking initiated on either surface of the tube wall.

The scanning device is configured to enable quick change out of probes and ultrasonic (UT) waveguides (also sometimes termed a wedge), such that multiple inspections of tubes having different diameters are expeditiously facilitated. The configuration of the scanning device also allows for smooth operation, thereby eliminating or minimizing chatter or skew, as will be described further herein.

The portable scanning device comprises a housing which contains a waveguide assembly for transmitting to and receiving ultrasonic signals from a waterwall tube, a magnet and screw assembly for adjusting the magnetic strength for holding the scanning device to the waterwall tube, and an encoder assembly for measuring the distance traversed (by the scanning device) along the tube and correlating this distance with any detected cracks. Also contained in the housing are associated supporting and operating mechanisms for the waveguide assembly, the magnet and screw assembly and the encoder assembly.

Figure 1B:
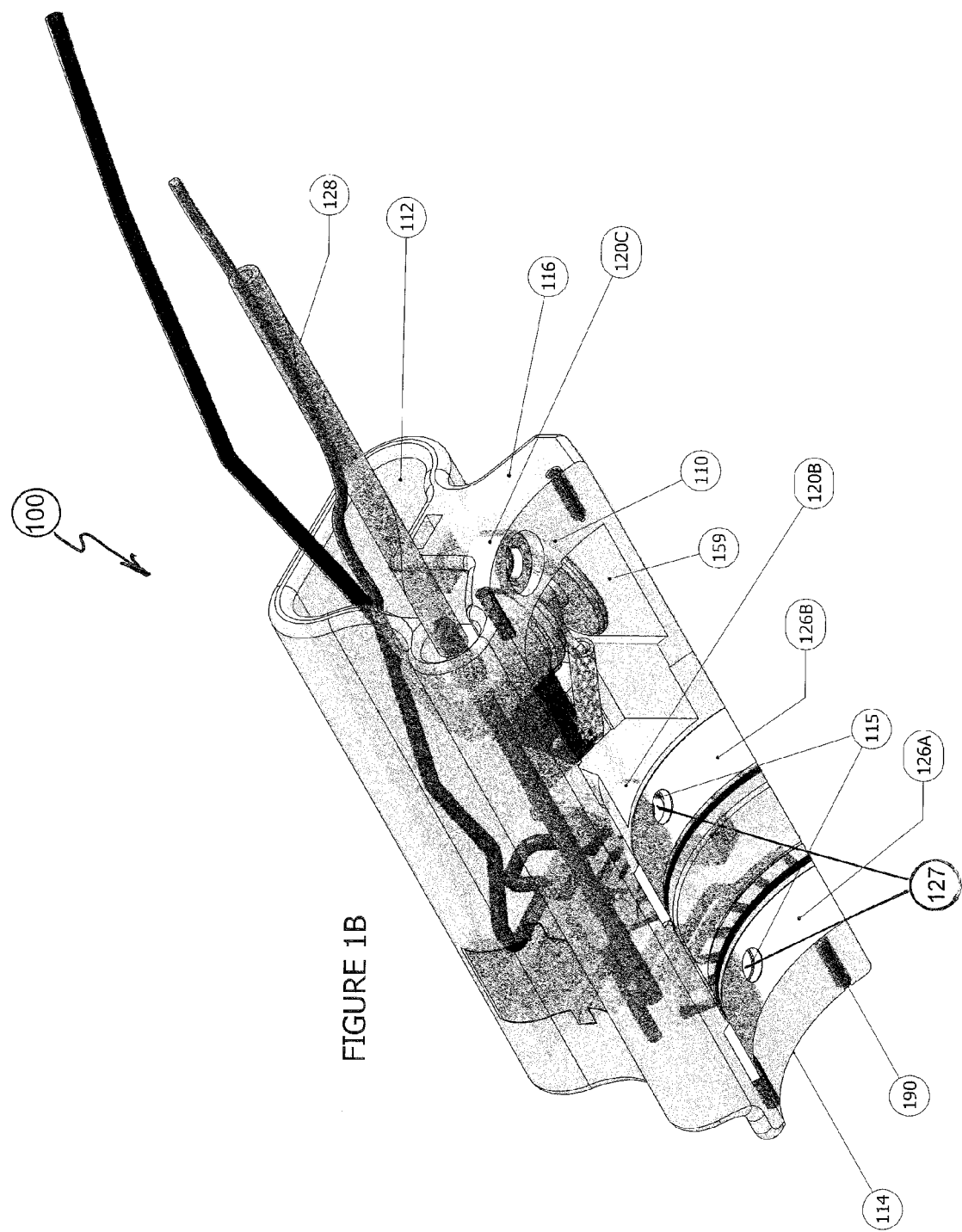
FIG. 1B is another isometric bottom view of an exemplary scanning device.

Turning now to FIGS. 1A and 1B, a portable scanning device 100 for performing nondestructive testing of tubes will now be described in accordance with exemplary embodiments. The FIGS. 1A and 1B are isometric views of an exemplary portable scanning device 100. The FIG. 1A is an isometric side view, while the FIG. 1B is an isometric bottom view. The portable scanning device 100 includes a housing 102 having a top surface 104 and a bottom surface 110. The bottom surface 110 is opposed to the top surface 104. The portable scanning device 100 also has opposing sidewalls 106 and 108 extending downward from two edges of the top surface.

In one embodiment, the housing 102 does not have a handle to permit one to hold the scanning device. The top surface 104 and sidewalls 106, 108 are designed so that the housing 102 can be held and manipulated by hand without having a discrete handle. The shape of the housing 102 enables testing personnel to manually guide the scanning device 100 on a tube to be tested for cracks. It is generally desirable for the housing 102 to be light weight so that it can be transported and manipulated manually by hand. It is also desirable for the housing to be manufactured from a material that can withstand moderately high temperatures of up to about 110° F., if indeed it turns out to be desirable to make measurements in a slightly elevated temperature environment. The housing 102 can be manufactured from a metal, a ceramic, or a polymer. When the housing 102 is manufactured from a polymer or from a ceramic, it is desirable for the polymer or the ceramic to be impact toughened so that the scanning device does not undergo cracking or chipping if it is dropped. In an exemplary embodiment, the housing 102 is manufactured from a polymer. Exemplary polymers are wood, a thermoplastic polymer or a thermosetting resin.

Exemplary thermoplastic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysiloxanes, polyurethanes, or the like, or a combination comprising at least one of the fore going thermoplastic polymers.

Exemplary thermosetting polymers are polyurethanes, natural rubber, synthetic rubber, epoxies, phenolics, polyesters, polyamides, silicones, or the like, or a combination comprising at least one of the foregoing thermosetting resins. Blends of thermoset resins as well as blends of thermoplastic resins with thermosets can be utilized.

Figure 2:
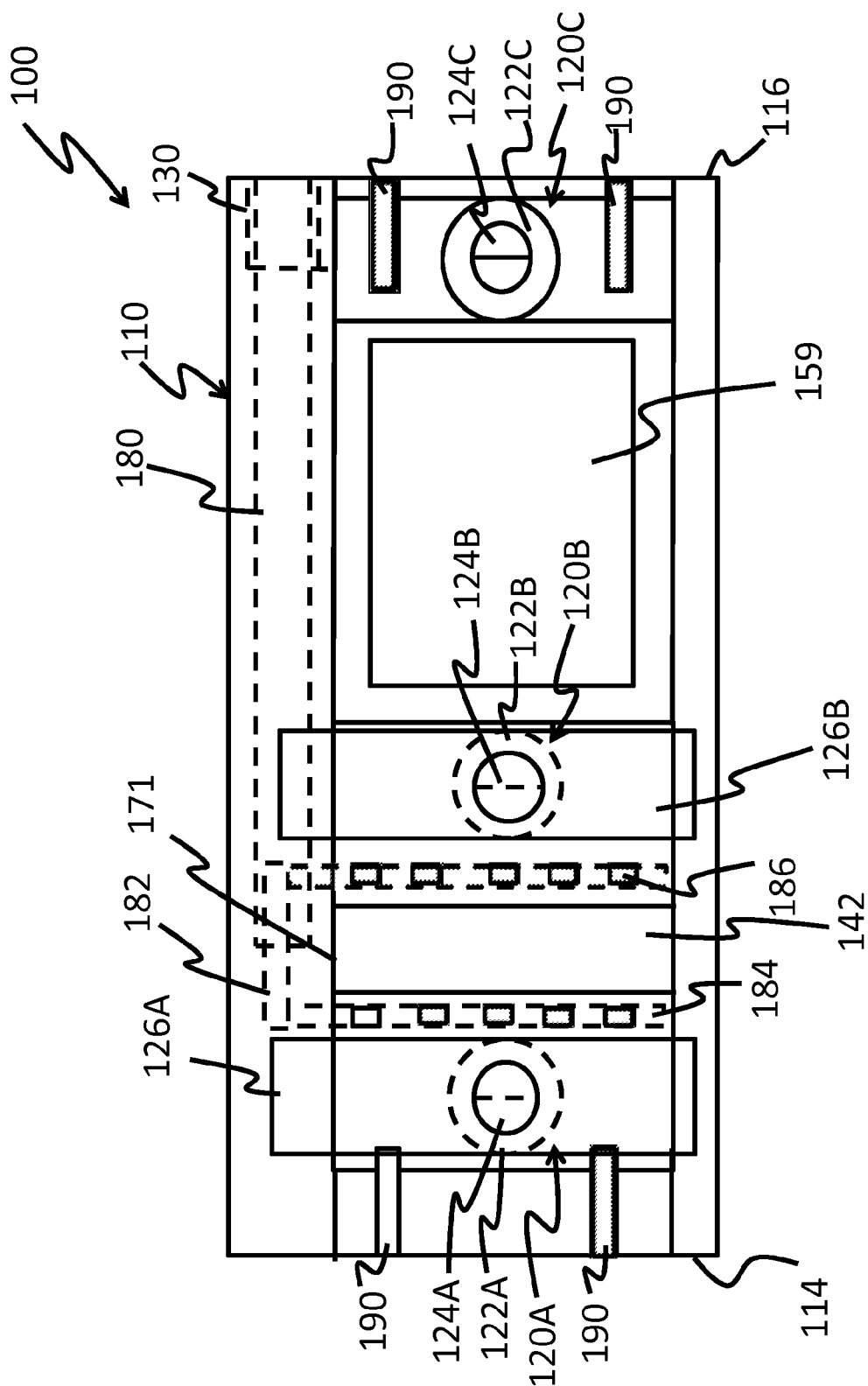
FIG. 2 is a view of the bottom surface of the housing with only the magnet and screw assemblies and the waveguide assembly disposed in the exemplary housing.

FIG. 2 is a depiction of the bottom surface 110 of the housing 102. As can be seen from FIGS. 1A and 1B, the bottom surface 110 is a concave curved surface for smooth motion across the outer surface of the waterwall tubes. The curvature of the bottom surface 110 is concave to accommodate the convex curvature of the tube outer surface. The housing 102 has openings 115 (See FIGS. 1B and 2) at its bottom surface 110 to accommodate the magnet and screw assemblies 120A, 120B and 120C, an opening 171 to accommodate the waveguide assembly 140 (See FIG. 2.) and an opening 159 to accommodate the encoder assembly 160 (See FIGS. 1B and 2.). The view of the bottom surface in the FIG. 2 (and the cross-sectional side view in the FIG. 3D) depicts three magnet and screw assemblies 120A, 120B and 120C, each of which are depicted in a dotted ellipse. The first magnet and screw assembly 120A is located proximate to the first end 114, while the second magnet and screw assembly 120B is located farther away from the first end 114. The first magnet and screw assembly 120A and the second magnet and screw assembly 120B are located on opposite sides of the waveguide assembly 140. The third magnet and screw assembly 120C lies proximate to the second end 116 of the housing 102. Located between the second magnet and screw assembly 120B and the third magnet and screw assembly 120C is a cavity 159 that houses the encoder assembly 160 (which is detailed later with respect to the FIG. 3D).

Each magnet and screw assembly comprises a cylindrically shaped magnet 122 (122A, 122B and 122C corresponding to assemblies 120A, 120B and 120C respectively) and a screw 124 (124A, 124B and 124C corresponding to assemblies 120A, 120B and 120C respectively), which is adjustably threaded to a nut 132 (132A, 132B and 132C corresponding to assemblies 120A, 120B and 120C respectively) contained in a space in the housing 102. The space for the nut has a geometrical shape that corresponds to the outer surface of the nut 132. The nut 132 therefore cannot rotate in the space that holds it in position. Each magnet 122 has a hole at its geometrical center through which passes the screw 124. The screw 124 then passes through the housing and is threaded by the nut 132. By rotating the screws 124A, 124B and 124C in the nuts 132A, 132B and 132C respectively, the position of the respective magnets 122A, 122B and 122C relative to the bottom surface 110 of the housing 102 can be adjusted. The magnets 122A, 122B and/or 122C can thus be moved closer to or further away from the tubes of the waterwall in the radial direction (where the radial distance is measured from the center of the tubes). By moving the magnets closer to or further away from the tubes, the attractive force exerted by the magnet on the tube can be changed to provide the desired force to hold the scanning device 100 onto the tube 200 (see FIG. 3A), while at the same time allowing the scanning device 100 to easily slide along the tube. The magnets also allow the user to keep the probe attached to the tube to allow the user to reposition without losing the encoder position reference.

Referring to the FIGS. 1B, 2 and 3D, disposed upon the bottom surface 110 of the housing 102 are at least two strips of soft absorbent material—a first strip 126A and a second strip 1 126B that can absorb and discharge a liquid (hereinafter a couplant). The first strip of absorbent material 126A and the second strip of absorbent material 126B are bonded to the bottom surface 110 of the housing 102. The first strip of absorbent material 126A and the second layer of absorbent material 126B partially cover the first magnet 122A and the second magnet 122B respectively. Each layer of absorbent material 126A and 126B includes an opening 127 (See FIG. 1B.) to permit access to the screws 124A and 124B respectively for adjustment.

In addition to absorbing and desorbing the couplant, the first strip of absorbent material 126A and the second strip of absorbent material 126B also act as seals to capture or to retain a film of couplant between the first strip 126A and the second strip 126B respectively, while the scanning device 100 is moved over the surface of a tube. The film of couplant lies between the waveguide 142 and the tubes that are being inspected for cracks and facilitates coupling of ultrasonic signals between the waveguide 142 and the tube. The couplant is supplied to the region between the waveguide 142 and the tube through a couplant tube 128 (See FIG. 1A.) and through a couplant manifold 130 (See FIG. 3B.). The couplant manifold 130 is in fluid communication with a plurality of ports 186 in the bottom surface via tubes 180, 182 and 184 contained or formed in the housing 102. The ports 186 are disposed in the housing 102 at the bottom surface 110 and lie on either side of the waveguide 142 of the waveguide assembly 140. While the figure shows two rows of ports 186, it is to be noted that a single row may be sufficient.

A couplant is continuously discharged from the ports 186 on the bottom surface 110 of the housing 102 when the scanning device 100 is being operated. The tubes 180, 182 and 184 of the manifold 130 are molded as part of the housing 102 during the manufacturing of the housing 102 by additive manufacturing, which is discussed below.

The couplant tube 128 has a first end connected to a couplant supply source (e.g., pressurized container or pump—not shown here) and a second end connected to a couplant manifold 130 disposed at the second end 116 of the housing 102. The couplant tube 128 receives couplant from the supply source (not shown) and delivers the couplant to the couplant manifold 130 (e.g., via a barbed fitting), which in turn, delivers the couplant directly to a plurality of ports 186 located at the bottom surface 110 of the housing 102. The couplant forms a layer (referred to herein as a "film") between the waveguide 142 and the tube to be examined and between the first and second strips of absorbent material 126A and 126B. It is through this couplant film that the ultrasonic signals are directed to the tube from the waveguide 142. The couplant material may be water, an organic solvent or a gel. In an exemplary embodiment, the couplant is water.

The soft absorbent material can comprise a fibrous material or a porous material that is capable of absorbing and desorbing a liquid. The fibrous material may be a weave or a non-woven fibrous strip (e.g., felt) that comprises a polymer. The porous material may also be a polymeric foam. The polymeric foam has an average pore size of 1 to 1,000 micrometers. Exemplary polymeric foams comprise cellulose, polyurethanes, polyacrylates, or the like. In an exemplary embodiment, the soft absorbent material is felt. An adhesive may be used to bond the strip of soft absorbent material 126A and 126B onto the bottom surface 110 of the housing 102.

Figure 3A:
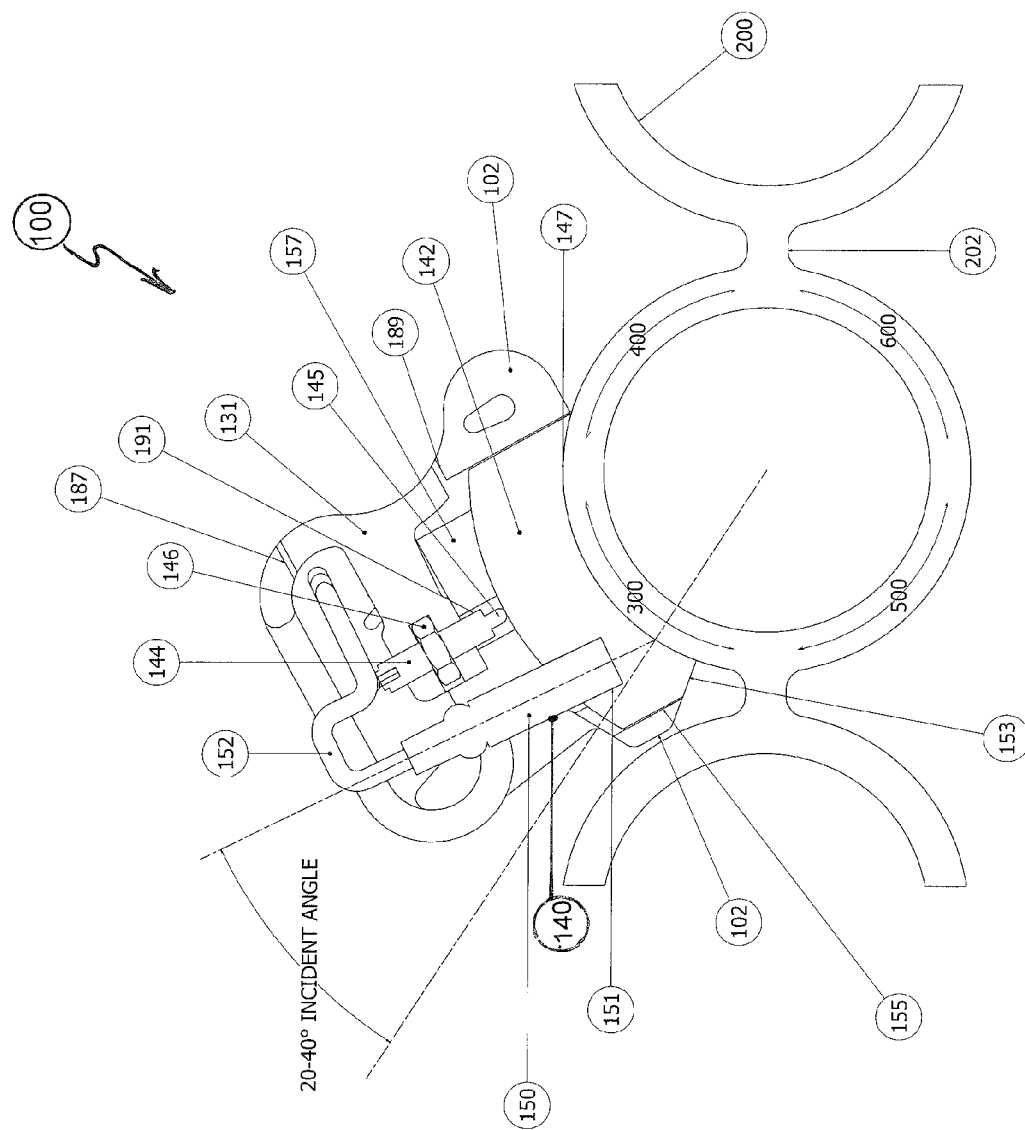
FIG. 3A is a sectional view taken along section A-A of the FIG. 1A.
Figure 3B:
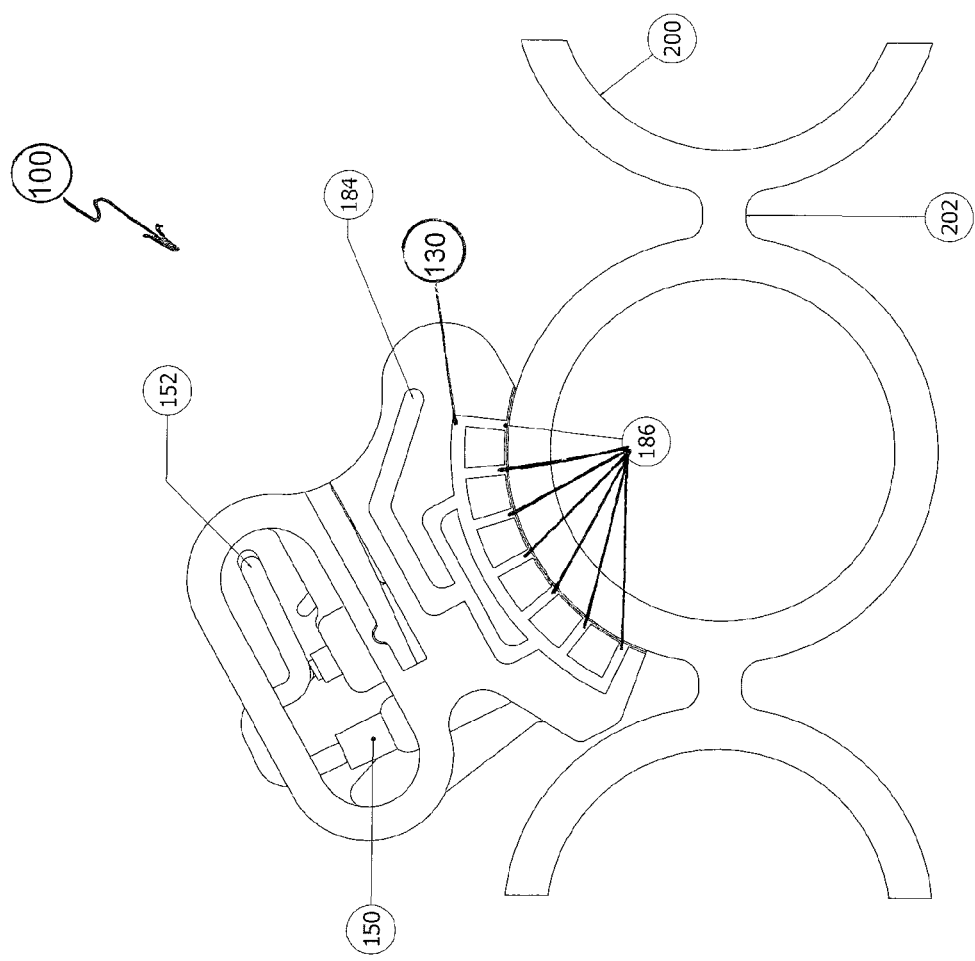
FIG. 3B is a sectional view taken along section B-B of the FIG. 1A.
Figure 3C:
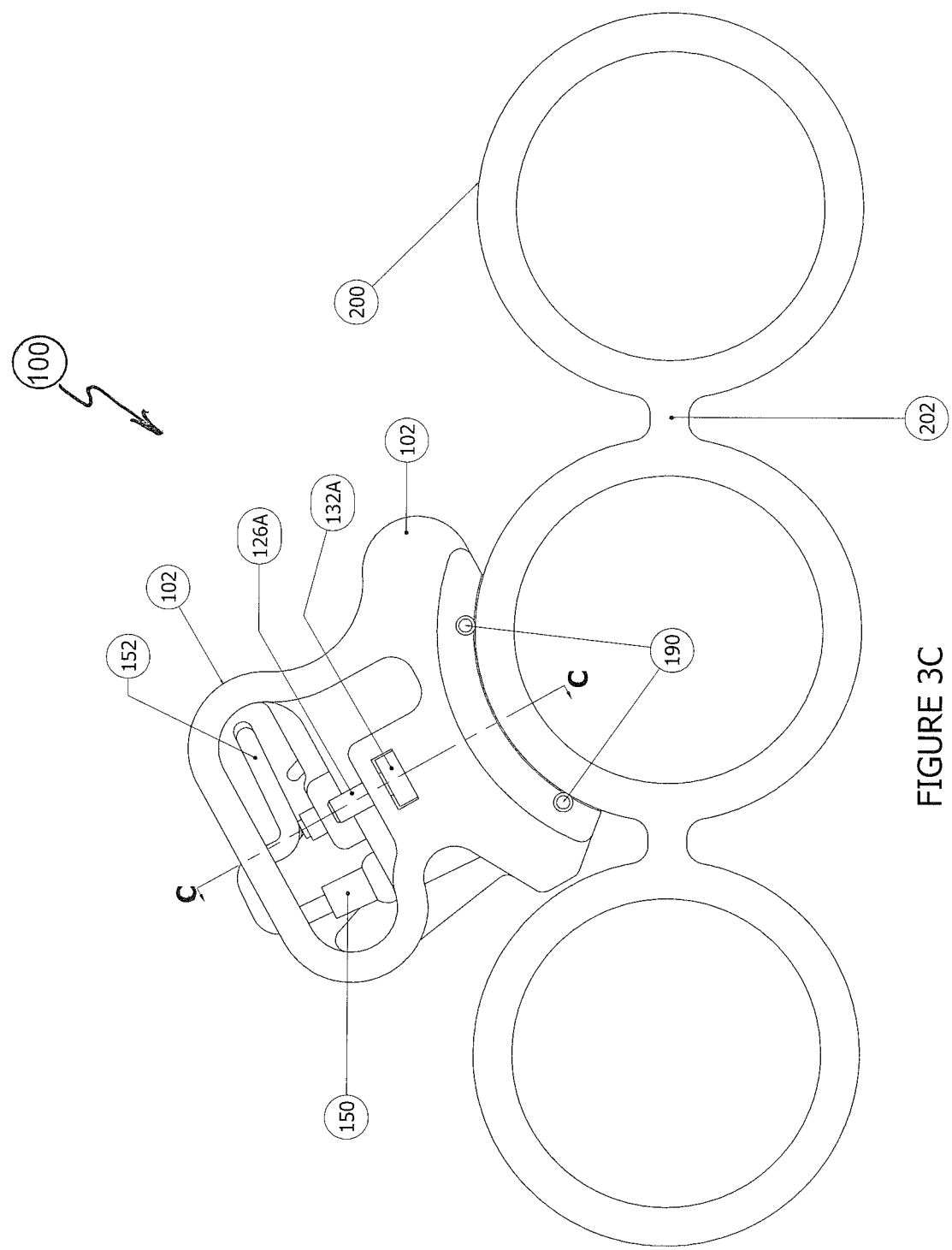
FIG. 3C is an end view of the exemplary scanning device.
Figure 3D:
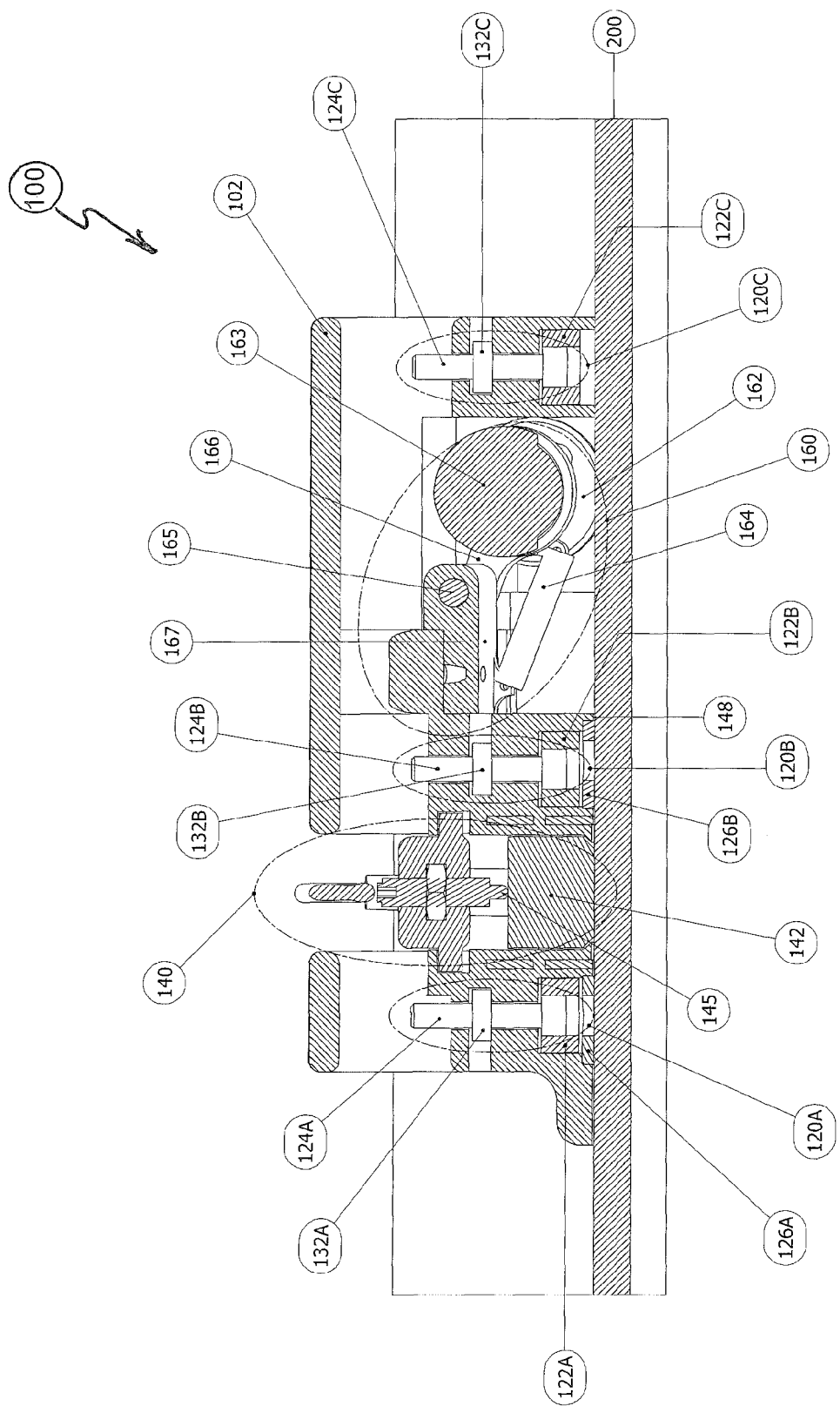
FIG. 3D is a sectional view taken along section C-C of the FIG. 3C.

Details of the waveguide assembly 140 and the encoder assembly 160 will now be provided with reference to FIGS. 3A-3D, which are sectional views obtained from the FIG. 1A. The FIG. 3A depicts a section taken at A-A in the FIG. 1A, while the Figure BB depicts a section taken at B-B in the FIG. 1A. The FIG. 3C is an end view of the scanning device 100 showing a section C-C, which is depicted in the FIG. 3D. The FIG. 3D is another exemplary embodiment, of an end view of the housing 102 taken with the waveguide assembly 140 and the encoder assembly 160 assembled in the housing 102 of the scanning device 100.

FIG. 3A is a depiction of section A-A (from the FIG. 1A) and displays the waveguide assembly 140 disposed between the first and the second magnet and screw assemblies 120A and 120B is the waveguide assembly 140. The waveguide assembly 140 facilitates the transmitting and receiving of ultrasonic signals into a waterwall tube and from the waterwall tube respectively. The waveguide assembly 140 comprises a waveguide 142 in contact with a probe 150. The probe 150 is an ultrasonic transducer that transmits and receives a phased array of ultrasonic waves (referred to herein as "signals"). In one embodiment, the surface 141 of the waveguide 142 that contacts the tube is concave so that it can contact the convex outer surface of the tube. The contact surface 141 of the waveguide 142 is contoured or curved to contact the tube surface as closely as possible. The lower side surface 153 of the waveguide 142 proximate to the probe 150 is tapered away from the housing 102 to minimize reflection of the ultrasonic signals back towards the probe and to prevent interference of the ultrasonic signals. The side surfaces 153 and 155 of the waveguide 142 are also textured to minimize reflection of the ultrasonic signals from these surfaces back to the probe 150. In one embodiment, the side surfaces 153 and 155 of the waveguide 142 are serrated (e.g., have a saw tooth shape) to minimize reflection of the ultrasonic signals back to the probe 150.

The arcuate length of the waveguide 142 is much larger than a side of the cross-sectional area of the probe. This increased arcuate length of the waveguide 142 provides strength and stability to the waveguide assembly 140 in the housing 102. The couplant facilitates contact between the concave surface of the waveguide 142 and the outer convex surface of the tube 200 so that ultrasonic signals may be introduced into the tube 200 and signals may be received from the tube 200.

The waveguide assembly 140 (which comprises the waveguide 142, the probe 150 and the cable 152) can be removed through the upper surface 104 of the waveguide by removing a slidable holder 131 that is located in the housing 102. The slidable holder 131 is manufactured from a polymer and contains a groove 191 that houses a screw 144. The screw has at its bottom a spring loaded ball 145. The spring loaded ball 145 snap fits into a notch contained in the upper surface (the surface opposed to the surface 141 that contacts the tube 200) of the waveguide 142. The screw 144 is adjustably threaded to a nut 146 and facilitates radially moving the waveguide 142 in the housing 102. The waveguide 142 may be moved closer to or farther away from the tube 200 (that is being examined) by rotating the nut 146.

The slidable holder 131 can be inserted into the housing 102 (by sliding) and removed from the housing by virtue of grooves 187 and 189. When in position, the slidable holder 131 is supported by a block 157 that is an integral part of the housing 102.

In order to insert the waveguide assembly 142 into the housing 102, the slidable holder 131 is first removed by sliding it out of the housing along grooves 187 and 189. The waveguide assembly 140 comprising the waveguide 142, the probe 150 and the cable 152 is then inserted into the housing 102 through a cavity in the upper surface 104. The slidable holder 131 is then slid back into the housing 102, wherein the spring loaded ball 145 snaps into a slot in the waveguide 142 thus holding the waveguide assembly 140 in position.

When it is desired to remove the waveguide assembly 142 from the housing 102, the waveguide 140 is extracted from the spring loaded ball 145 by pulling the waveguide 140 away from the slidable holder 131. The slidable holder 131 is then slid out of the housing via grooves 187 and 189. The waveguide assembly 142 is then removed from the housing 102 via an opening in the upper surface of the housing 102.

The waveguide 142 comprises an optically transparent piece of plastic. The optically transparent piece of plastic comprises a polyester, a polymethylmethacrylate, a polycarbonate, a polystyrene, a crosslinked styrene copolymer, a polyetherimide, or the like, or a combination comprising at least one of the foregoing pieces of plastic. In one embodiment, the waveguide is machined from REXOLITE® (a crosslinked styrene copolymer) or from LUCITE® (a polymethylmethacrylate), which have suitable acoustic properties.

The waveguide has a slot 151 that accommodates the probe 150. In one embodiment, the portion of the waveguide 142 between the probe 150 and the tube 200 guides the ultrasonic signals towards the tube.

As detailed above, it is desirable to use a waveguide 142 whose concave surface is contoured to match the outer convex surface of the waterwall tubes 200. It may thus be desirable to replace a waveguide 142 used for one set of tubes with another waveguide for another set of tubes, whose radii are different from those of the previous set of tubes. The waveguide may thus be easily replaced by removing it from the spring loaded ball 145 and snapping a new waveguide (having a different contoured surface) into position in its place using the spring loaded ball 145. While replacing an existing waveguide 142 with a new waveguide 142, the probe 150 is first removed from the existing waveguide 142. A couplant is added to the slot 151 of the new waveguide 142, prior to pressure fitting the probe 150 into the new waveguide 142. The new waveguide 142 is then snapped into position (using the spring loaded ball 145) in the housing 102.

Advantageously, a surface 147 of the waveguide 142 is contoured or curved to the outer circumference of the tube 200, thus allowing a portion of the tube 200 circumference to be scanned. For example, if the tube 200 has a 2.5-inch diameter, the waveguide 142 selected for use with the scanning device 100 will have about a 1.25 inch contoured radius. This is particularly advantageous where tube 200 is part of a waterwall, as depicted in the FIG. 2A. In a waterwall, tubes 200 are coupled in side-by-side fashion by welded webs (membranes) 202. In one embodiment, the contour of the waveguide 142 allows a probe 150 to scan substantially the entire portion of the tube 200 from the web 202 on one side of the tube 200 to web 202 on the other side of the tube 200.

The probe 150 is in operative communication with the waveguide 142. A slot 151 in the upper surface of the waveguide 142 accommodates the probe 150 and holds the probe at a fixed known orientation and angle of incidence to the outer surface of the tube 200. The slot 151 may be molded during the manufacturing of the waveguide 142 or alternatively may be machined into the waveguide 142. The probe 150 can be attached and detached from the waveguide 142. As noted above it is pressure fit into the waveguide 142. Some couplant may be used in the slot 151 to facilitate proper signal transmission between the probe 150 and the waveguide 142.

The detachability of the probe 150 provides for quick change out of the various waveguide 142 sizes that may be required for the varying sizes of tubes under inspection. The probe 150 transmits sound waves in the ultrasound frequency range through the waveguide 142 into the tube 200. The transmitted sound is in a phase array signal which transmits ultrasonic signals at varying angles.

Figure 4:
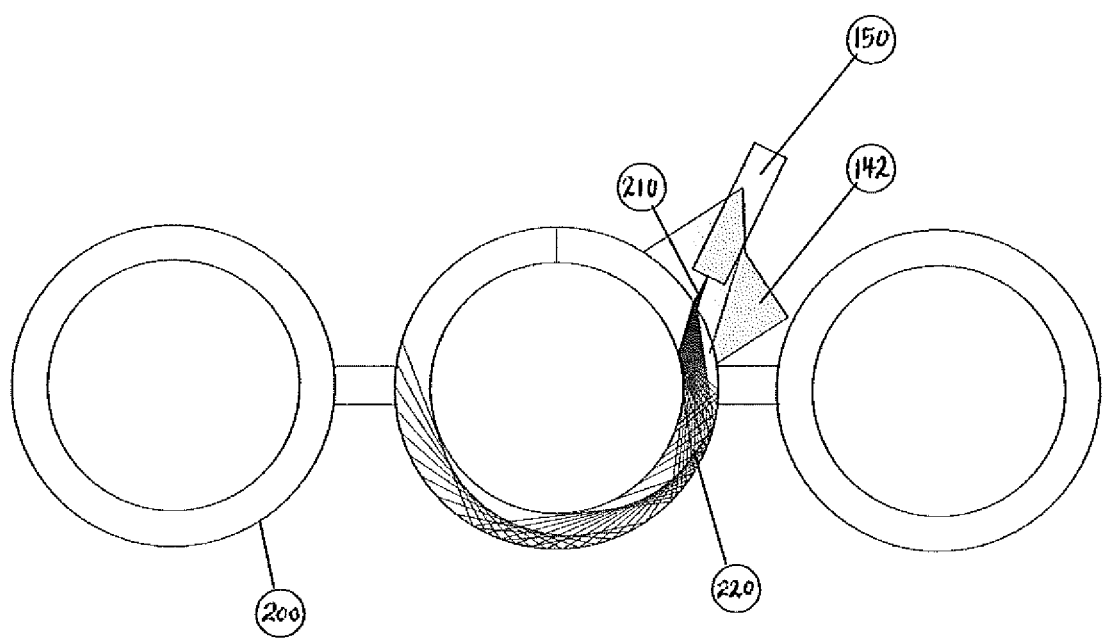
FIG. 4 is a sectional view showing the sound traveling through the tube wall.

The probe 150 generally has a square cross-sectional area, but may have other geometrical cross-sectional areas (e.g., circular, triangular, polygonal, and the like) as well. The position of the probe 150 in the waveguide 142 is fixed in a predetermined orientation and angle so that ultrasonic signals may be introduced into the hot side of a tube wall and travel circumferentially in the cold side of a tube wall. As can be seen in the FIG. 3A, the probe 150 is located at an incident angle of 20 to 40 degrees with respect to two lines—a first line that passes through the center of the cross-sectional area of the probe 150 and a line that passes through the center of the tube 200 (that is being examined) and the point at which the ultrasonic signals contact the surface of the tube 200. This angle between the first line and the second line is termed the angle of incidence. By adjusting the angle of incidence to be between 20 to 40 degrees, the sound waves obey Snell's law and are refracted into the tube 200 and travel in the circumferential direction as shown in the FIG. 4. The probe 150 is disposed off-center in the waveguide 142 to get the signal as close to the membrane 202 of the waterwall as possible (See FIG. 3A.).

The probe 150 includes a cable 152 extending therefrom (See FIG. 1A.). The cable 152 is operative to transmit electrical signals between the probe 150 and an ultrasonic puller and receiver (not shown) and a computing device (also not shown) (e.g., a general purpose computer, signal processor or analyzer) having memory to record the electrical signals received from the probe 150. The computing device processes the received information and has a display screen to allow an operator to view a visual indication of the electrical signals received from the probe 150. Using various applications, the data acquired and recorded from the inspection may be converted in graphical form and displayed by the computing device. The graphical form of the data may illustrate qualitative and quantitative results of the inspections via the ultrasonic probe 150. For example, the results may include defects in the tube wall under inspection, as well as the extent of the defects (such as size, range, and depth). The scanning device in the FIG. 2C is depicted being disposed upon a waterwall tube comprising a plurality of tubes 200 that are held together by a membrane 202 that is welded to the respective tubes 200.

In one embodiment, the probe 150 comprises a phased array of ultrasonic transmitters and sensors. The phased array utilizes a linear or two-dimensional array of ultrasonic transducers that are sequentially pulsed in sequence. Through superposition of individual wavelets, phased arrays provide the capability of steering the angle of the beam. Thus, the beam angle may be set by adjusting the timing of the individual pulses. By having the ability to sweep through multiple angles, an increase in detectability can be realized.

The scanning device 100 also comprises an encoder assembly 160 that is housed in the cavity 159 of the housing 102 (See FIG. 2.) and is operative to provide a reference point for a physical location on the pipe 200 at which the inspection is initiated, as well as a means for tracking and recording the responses from the probe 150 with respect to the ongoing inspection. The encoder assembly 160 may be located at any place on the bottom surface 110 of the scanning device 100. In an exemplary embodiment the encoder assembly 160 is located on the side of the second magnet and screw assembly 120B that is opposed to the side that faces the waveguide assembly 140.

In the FIG. 3D, the encoder assembly 160 includes an encoder 163 in communication with a wheel 162 that rests on the tube 200 and rotates as the scanning device 100 is moved relative to the tube 200. The encoder assembly 160 is held in place by a bracket 167 that is part of the housing 102. The wheel 162 and the encoder 163 are mounted on a shaft (not shown) that is suspended at the opposite end of a cantilever beam 166 that pivots on a shaft 165 housed on the bracket 167. The wheel 162 is spring loaded with a spring 164 that forces the wheel 162 towards the tube to contact the surface of the tube 200. The spring 164 may be a cantilever spring, which has one end contacting the bracket 167, while the other end contacts the shaft on which the wheel 162 is mounted. Other forms of springs (e.g., leaf springs, coil springs, and the like) may also be used. The spring 164 prevents the scanning device 100 from being moved over the tubes 200 without the wheel 162 being rotated and thus not recording the movement. A sensor within the encoder 163 detects rotation of the wheel, which indicates the relative position of the probe 150 as it moves along the tube 200. The encoder 163 provides electrical signals indicative of this position to the computer device via cable 166, thus allowing the computer device to correlate probe 150 readings with specific locations on tube 200.

The scanning device 100 also comprises a plurality of hardened wear pins 190 (See FIGS. 1A and 2.) that are disposed on the bottom surface 110 proximate to the first end and second end of the scanning device to prevent damage to the waveguide. The hardened wear pins 190 can be manufactured from carbides. In one embodiment, at least a pair of carbide wear pins are disposed at the on the bottom surface 110 at the first end 114 and another pair of carbide wear pins are disposed on the bottom surface 110 at the second end 116.

During operation of the scanning device 100, the waveguide 142 contacts the tube 200 via a couplant, as described hereinafter. In an exemplary embodiment, the waveguide 142 may be arranged to scan in a direction generally parallel to longitudinal axis of the tube 200. The longitudinal axis of the tube 200 is perpendicular to the plane of the paper in the FIG. 3A. The scanning device 100 is moved along the surface of the tube 200 (on the hot side of the waterwall) along the longitudinal axis of the tube. The scanning device 100 is moved along the surface of the tube 200 as close as possible to the membrane 202 (See FIG. 3A.) to obtain a scan of at least a quadrant (90 degrees) of the tube that lies on the opposite side of the membrane but on the same side of the tube as the side on which the scan is conducted. With reference to the FIG. 4, the ultrasound signal is introduced into the wall of the tube 200 at a predetermined angle, which is determined by the geometry and characteristics of the tube, i.e., the radius, the material, the wall thickness, and the like.

The ultrasonic signals 210 are refracted through the waveguide 142 and travel through the tube wall past the membrane 202 in the circumferential direction. Due to Snell's law, the angle of the signal may refract about 10 degrees additionally when passing into the tube wall. The ultrasonic signals 210 travel through the tube wall in the circumferential direction as shown in the FIG. 4 and are represented by numeral 220. Electronic sweeping of the beam assists in getting sound past the membrane and allows for improved direction by interacting with the cracking more perpendicularly. When a section of the tube 200 contains no crack, the beam travels through the tube wall and produces a background spectrum (that does not contain any peaks) on the computer screen. When the signal encounters a crack in the tube wall, the sound is reflected back along the path it travels and is received by the waveguide 142 and the probe 150 and is provided to a computer via the cable 152. A computer screen displays a spectrum containing higher amplitude peaks (that can be distinguished from the background spectrum) from which the location and approximate size of the crack can be detected. Cracks can be detected by this method. In one embodiment in order to completely scan the cold side of the tube 200 for cracks, the scanning device 100 is rotated 180 degrees and is then traversed along the tube 200 (again on the hot side) in the opposite direction from the direction in which it was previously traversed on the other side of the tube 200. It is to be noted that by using ultrasonic signals or signals having a greater intensity, the entire cold side of the tube 200 can be scanned for cracks in a single scan along one side of the tube 200.

The method for determining crack location in the tube 200 will now be detailed with reference to the FIG. 3A. In order to determine the crack location in the quadrant 500 of the tube 200, the scanning device is moved along the quadrant 300 of the tube. The ultrasonic signals (signals) traverse counterclockwise past the membrane 202 of the tube 200, and if any cracks are present in the quadrant 500, the signals are reflected back and displayed on the computer screen. In order to determine the crack location in the quadrant 600 of the same tube 200, the scanning device is moved along the quadrant 400 of the tube. The ultrasonic signals traverse clockwise past the membrane 202 of the tube 200, and if any cracks are present in the quadrant 600, the signals are reflected back and are displayed on the computer screen. A two-dimensional or three-dimensional view of the scanned portion of the tube may be displayed on the computer screen.

In one embodiment, in one method of manufacturing the scanning device 100, the housing 102 is first printed by a method that comprises additive manufacturing. The additive manufacturing is also termed 3-D manufacturing. The housing 102 is manufactured such that it contains cavities for housing the magnet and screw assemblies 120A, 120B and 120C. The housing 102 also contains cavities that house the waveguide assembly 140 and the encoder assembly 160. The tubes 180, 182 and 184 for transporting the couplant are also integrally contained in the housing 102. In other words the tubes 180, 182 and 184 are formed in the housing and are not inserted separately into the housing.

The magnet and screw assemblies 120A, 120B and 120C are then affixed to the housing 102. The strips of soft absorbent material 126A and 126B (e.g., felt) are then bonded to the housing 102. The waveguide assembly 140 and the encoder assembly 160 are then affixed to the housing 102. The carbide wear pins may then be disposed in the third magnet and screw assembly 120C and in the curved bottom surface of the housing 102 respectively. The position of the magnet and screw assemblies and the waveguide assembly can be adjusted by turning the nut on the screw for each of these assemblies. The conduits and electrical supply are then connected to the housing 102 in their respective positions that are detailed above.

The scanning device and the method disclosed herein have a number of advantages. The scanning device is printed using additive manufacturing techniques (also known as 3-dimensional printing or rapid prototyping), which makes them lightweight, compact, ergonomic and comfortable. The scanning device is printed with specific curvatures that match the outer diameter of the waterwall tubes. The scanning device has an encoder that has a spring loaded wheel to prevent slippage while being displaced along the outer surface of the waterwall tubes thus allowing for determining accurate axial position on tube. The scanning device has self-contained water channels and passages for couplant delivery to the probe. It has felt inserts, which help with tube wetting and containment of couplant. It also has carbide wear pins to limit probe waveguide wear.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, singular forms like "a," or "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The term and/or is used herein to mean both "and" as well as "or". For example, "A and/or B" is construed to mean A, B or A and B.

The transition term "comprising" is inclusive of the transition terms "consisting essentially of" and "consisting of" and can be interchanged for "comprising".

While this disclosure describes exemplary embodiments, it will be understood by those skilled in the art that various changes can be made and equivalents can be substituted for elements thereof without departing from the scope of the disclosed embodiments. In addition, many modifications can be made to adapt a particular situation or material to the teachings of this disclosure without departing from the essential scope thereof. Therefore, it is intended that this disclosure not be limited to the particular embodiment disclosed as the best mode contemplated for carrying out this disclosure.

What is claimed is:

1. A scanning device for performing ultrasonic nondestructive testing of a tube, comprising:
    a housing; the housing having a bottom surface that is concavely curved with cavities to accommodate a waveguide assembly and an encoder assembly; and
    a magnet and screw assembly affixed to the housing and including a magnet and a screw, wherein a radial distance of the magnet relative to the bottom surface of the housing and a center of the tube is selectively adjustable via the screw to adjust an attractive force of the magnet on the tube;
    where the waveguide assembly comprises a waveguide and a probe that are in communication with one another; the waveguide having at least one surface that is contoured to match an outer surface of the tube; where the waveguide facilitates the transmission of ultrasonic signals generated by the probe into the tube; where the probe contacts the waveguide at an angle of incidence of 20 to 40 degrees with respect to the probe centerline and a line that passes through the center of the tube and a point at which the ultrasonic signals contact the surface of the tube; where the waveguide is arranged to direct ultrasonic waves from the probe into a wall of the tube such that the waves travel within the wall of the tube along a circumferential direction of the tube; and
    where the encoder assembly comprises a spring loaded wheel that contacts the tube; and where the encoder assembly provides a signal indicative of a location of the probe relative to a position on the tube as the scanning device is moved in a direction of a longitudinal axis of the tube; where the scanning device is operative to detect cracks on a side of a waterwall while being positioned on an opposing side of the waterwall.

2. The scanning device of claim 1, further comprising two strips of soft absorbent material that contact the housing disposed on opposing sides of the waveguide assembly, where the soft absorbent material is operative to provide a film of a couplant between the waveguide and the tube; where the couplant is operative to transfer an ultrasound beam from the waveguide to the tube.

3. The scanning device of claim 2, where the magnet of the magnet and screw assembly is a cylindrical magnet and is operative to facilitate contact between the scanning device and a tube whose properties are to be measured.

4. The scanning device of claim 2, where the housing comprises a thermoplastic polymer, a thermosetting polymer or a combination thereof.

5. The scanning device of claim 3, where the housing comprises at least two magnet and screw assemblies and where the at least two magnet and screw assemblies are disposed on opposing sides of the waveguide assembly.

6. The scanning device of claim 2, where the housing comprises at least three magnet and screw assemblies, and where at least two of the magnet and screw assemblies are disposed directly on opposing sides of the waveguide assembly.

7. The scanning device of claim 2, where the soft absorbent material is felt.

8. The scanning device of claim 2, further comprising a couplant tube that is in fluid communication with the soft absorbent material.

9. The scanning device of claim 2, where the spring loaded wheel is operative to measure movement of the scanning device in a direction of a longitudinal axis of the tube.

10. The scanning device of claim 2, where the spring loaded wheel is mounted at the end of a cantilever arm.

11. The scanning device of claim 2, where the spring loaded wheel is in communication with an encoder that measures the position of the scanner with respect to the scanner's position on the tube.

12. The scanning device of claim 1, wherein the probe is a phased array probe.

13. The scanning device of claim 3, where rotating a screw on the magnet and screw assembly moves the magnet towards or away from the tube.

14. The scanning device of claim 1, where the waveguide comprises an optically transparent material.

15. The scanning device of claim 1, where the housing comprises ports disposed on at least one side of the waveguide assembly; the ports being operative to discharge a couplant.

16. The scanning device of claim 2, where a screw with a spring loaded ball is used to position the waveguide assembly in the housing.

17. The scanning device of claim 16, where a slidable holder houses the screw with the spring loaded ball.

18. The scanning device of claim 17, where the slidable holder is removable from the housing by sliding the slidable holder out of the housing.

* * * * *